United States Patent
Kadziauskas et al.

(10) Patent No.: US 9,072,599 B2
(45) Date of Patent: Jul. 7, 2015

(54) FIXATION OF OPHTHALMIC IMPLANTS

(75) Inventors: Kenneth E. Kadziauskas, Coto de Caza, CA (US); Carina R. Reisin, Tustin, CA (US); Timothy R. Bumbalough, Fullerton, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 478 days.

(21) Appl. No.: 12/870,570

(22) Filed: Aug. 27, 2010

(65) Prior Publication Data
US 2011/0054601 A1  Mar. 3, 2011

Related U.S. Application Data

(60) Provisional application No. 61/237,520, filed on Aug. 27, 2009.

(51) Int. Cl.
| | | |
|---|---|---|
| *A61F 2/16* | (2006.01) | |
| *A61F 9/007* | (2006.01) | |
| *A61F 2/00* | (2006.01) | |

(52) U.S. Cl.
CPC ............ *A61F 2/16* (2013.01); *A61F 2220/0016* (2013.01); *A61F 2/1635* (2013.01); *A61F 9/00781* (2013.01); *A61F 2002/009* (2013.01); *A61F 2250/0003* (2013.01)

(58) Field of Classification Search
CPC ............................. A61F 2/16–2/1689; A61F 2220/0008–2220/0016
USPC .............. 623/6.37–6.55, 6.22, 6.5, 6.16, 6.34
See application file for complete search history.

(56) References Cited

U.S. PATENT DOCUMENTS

| | | |
|---|---|---|
| 4,361,913 A | 12/1982 | Streck |
| 4,370,760 A | 2/1983 | Kelman |
| 4,373,218 A | 2/1983 | Schachar |
| 4,442,553 A | 4/1984 | Hessburg |
| 4,474,751 A | 10/1984 | Haslam et al. |

(Continued)

FOREIGN PATENT DOCUMENTS

| | | |
|---|---|---|
| CH | 681687 A5 | 5/1993 |
| EP | 766540 A1 | 4/1997 |

(Continued)

OTHER PUBLICATIONS

International Search Report for Application No. PCT/US2010/047011, mailed on Feb. 16, 2011, 7 pages.

(Continued)

*Primary Examiner* — Paul Prebilic
(74) *Attorney, Agent, or Firm* — Abbott Medical Optics Inc.

(57) ABSTRACT

An accommodating intraocular lens (aIOL) is disclosed, with an optic that changes shape in response to an ocular force exerted by the zonules of the eye. A haptic supports the optic around its equator and couples the optic to the capsular bag of the eye. A surface adherent improves the accommodative performance of the haptic, such that compressive/tensile forces may be more efficiently transferred from the haptic to optic. One way to enhance force transfer is to provide a surface layer of an adhesive to the haptic and/or optic, for instance a reversible bioadhesive material. Or, portions of the exterior surface of the IOL may have microfibers thereon that mimic the adhesive properties of Gecko feet. Another aspect is application of a reversible bioadhesive material to the interior of the empty capsular bag prior to introduction of an injectable polymer IOL.

6 Claims, 7 Drawing Sheets

(56) References Cited

U.S. PATENT DOCUMENTS

| | | |
|---|---|---|
| 4,474,752 A | 10/1984 | Haslam et al. |
| 4,474,753 A | 10/1984 | Haslam et al. |
| 4,478,822 A | 10/1984 | Haslam et al. |
| 4,512,040 A | 4/1985 | McClure |
| 4,542,542 A | 9/1985 | Wright |
| 4,560,383 A | 12/1985 | Leiske |
| 4,562,600 A | 1/1986 | Ginsberg et al. |
| 4,608,050 A | 8/1986 | Wright et al. |
| 4,615,701 A | 10/1986 | Woods |
| 4,641,934 A | 2/1987 | Freeman |
| 4,731,078 A | 3/1988 | Stoy et al. |
| 4,769,035 A | 9/1988 | Kelman |
| 4,813,955 A | 3/1989 | Achatz et al. |
| 4,842,601 A | 6/1989 | Smith |
| 4,865,601 A * | 9/1989 | Caldwell et al. ............ 623/5.14 |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,963,148 A | 10/1990 | Sulc et al. |
| 4,994,082 A | 2/1991 | Richards et al. |
| 4,994,083 A | 2/1991 | Sulc et al. |
| 5,002,571 A * | 3/1991 | O'Donnell et al. ......... 623/6.11 |
| 5,047,051 A | 9/1991 | Cumming |
| 5,133,748 A * | 7/1992 | Feaster ....................... 623/6.12 |
| 5,152,789 A | 10/1992 | Willis |
| 5,275,623 A | 1/1994 | Sarfarazi |
| 5,366,499 A * | 11/1994 | Py ............................... 623/5.15 |
| 5,476,445 A | 12/1995 | Baerveldt et al. |
| 5,476,514 A | 12/1995 | Cumming |
| 5,489,302 A | 2/1996 | Skottun |
| 5,496,366 A | 3/1996 | Cumming |
| 5,607,472 A | 3/1997 | Thompson |
| 5,628,795 A | 5/1997 | Langerman |
| 5,674,282 A | 10/1997 | Cumming |
| 5,984,962 A | 11/1999 | Anello et al. |
| 6,013,101 A | 1/2000 | Israel |
| 6,050,970 A | 4/2000 | Baerveldt |
| 6,051,024 A | 4/2000 | Cumming |
| 6,083,261 A | 7/2000 | Callahan et al. |
| 6,110,202 A | 8/2000 | Barraquer et al. |
| 6,117,171 A | 9/2000 | Skottun |
| 6,120,538 A | 9/2000 | Rizzo, III et al. |
| 6,197,059 B1 | 3/2001 | Cumming |
| 6,200,342 B1 | 3/2001 | Tassignon |
| 6,217,612 B1 | 4/2001 | Woods |
| 6,299,641 B1 | 10/2001 | Woods |
| 6,443,985 B1 | 9/2002 | Woods |
| 6,589,550 B1 | 7/2003 | Hodd et al. |
| 6,598,606 B2 | 7/2003 | Terwee et al. |
| 6,930,838 B2 | 8/2005 | Schachar |
| 6,942,695 B1 * | 9/2005 | Chapoy et al. ................ 623/6.5 |
| 7,097,660 B2 | 8/2006 | Portney |
| 7,150,759 B2 | 12/2006 | Paul et al. |
| 7,179,292 B2 | 2/2007 | Worst et al. |
| 7,182,780 B2 | 2/2007 | Terwee et al. |
| 7,220,279 B2 | 5/2007 | Nun |
| 7,344,617 B2 | 3/2008 | Dubrow |
| 7,503,938 B2 | 3/2009 | Phillips |
| 7,815,678 B2 | 10/2010 | Ben Nun |
| 2003/0004569 A1 | 1/2003 | Haefliger |
| 2003/0187505 A1 * | 10/2003 | Liao ............................ 623/6.37 |
| 2004/0082993 A1 | 4/2004 | Woods |
| 2004/0082995 A1 | 4/2004 | Woods |
| 2004/0111153 A1 | 6/2004 | Woods et al. |
| 2004/0162612 A1 * | 8/2004 | Portney et al. ............. 623/6.34 |
| 2005/0018504 A1 | 1/2005 | Marinelli et al. |
| 2005/0021139 A1 | 1/2005 | Shadduck |
| 2005/0021140 A1 * | 1/2005 | Liao ............................ 623/6.37 |
| 2005/0131535 A1 | 6/2005 | Woods |
| 2006/0238702 A1 | 10/2006 | Glick et al. |
| 2007/0078515 A1 | 4/2007 | Brady |
| 2007/0100444 A1 | 5/2007 | Brady et al. |
| 2007/0106381 A1 | 5/2007 | Blake |
| 2007/0129798 A1 | 6/2007 | Chawdhary |
| 2007/0135915 A1 | 6/2007 | Klima |
| 2007/0213817 A1 | 9/2007 | Esch et al. |
| 2007/0260309 A1 | 11/2007 | Richardson |
| 2007/0282247 A1 | 12/2007 | Desai et al. |
| 2008/0140192 A1 | 6/2008 | Humayun et al. |
| 2008/0161913 A1 | 7/2008 | Brady et al. |
| 2008/0161914 A1 | 7/2008 | Brady et al. |
| 2009/0012609 A1 | 1/2009 | Geraghty et al. |

FOREIGN PATENT DOCUMENTS

| | | | |
|---|---|---|---|
| EP | 766540 B1 | 8/1999 | |
| JP | 2126847 | 5/1990 | |
| WO | WO0119288 A1 | 3/2001 | |
| WO | WO0156510 A1 | 8/2001 | |
| WO | WO0219949 A2 | 3/2002 | |
| WO | WO2008108524 A1 | 9/2002 | |
| WO | WO2005115278 A1 | 12/2005 | |
| WO | WO 2008/108524 A1 * | 9/2008 | ............... A61F 2/16 |
| WO | WO02071983 A1 | 9/2008 | |

OTHER PUBLICATIONS

English translation of WO 93/05733 A1, (translation of abstract only), (Apr. 1993).

U.S. Appl. No. 09/656,661, filed Sep. 7, 2000.

U.S. Appl. No. 09/721,072, filed Nov. 22, 2000.

* cited by examiner

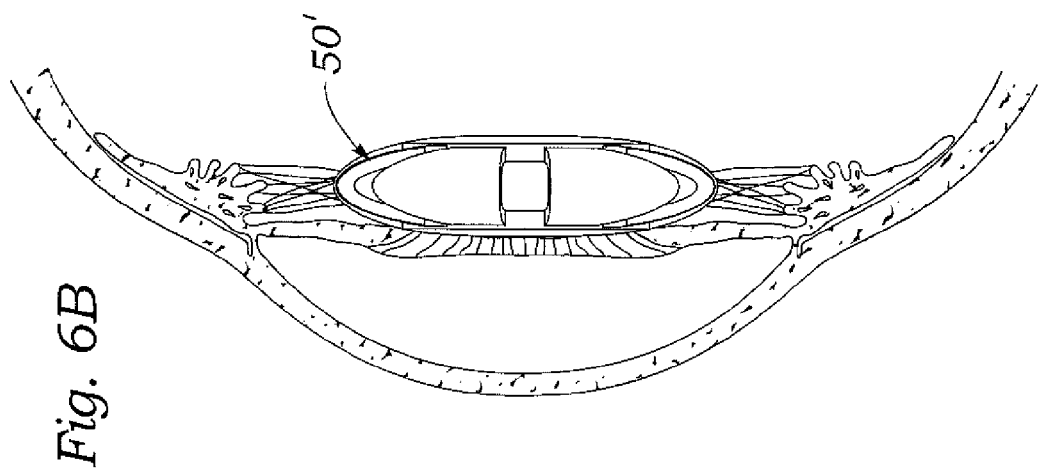
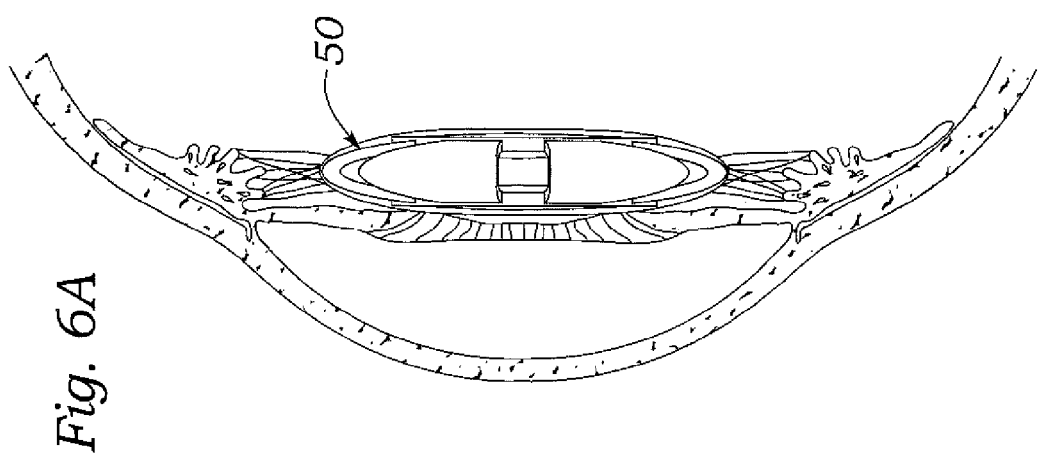

FIXATION OF OPHTHALMIC IMPLANTS

CLAIM OF PRIORITY

The present application claims priority under 35 U.S.C §119(e) to provisional application No. 61/237,520, filed on Aug. 27, 2009 under the same title, which is incorporated herein by reference in its entirety. Full Paris Convention priority is hereby expressly reserved.

FIELD OF THE INVENTION

The present invention relates to ophthalmic implants and related methods, and more particularly to intraocular lenses and glaucoma shunts with improved fixation and/or control of cellular growth.

BACKGROUND OF THE INVENTION

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. In other cases, glaucoma may result in a gradual and undesirable increase of intraocular pressure (IOP). In such instances, a shunt may be implanted to help control pressure within the eye. In either case, it is generally desirable to maintain the ocular device at a fixed location within the eye.

The simplest IOLs are monofocal IOLs that are fixed within the eye and have a single focal length or power. Unlike the eye's natural lens, which can adjust its focal length within a particular range in a process known as accommodation, these IOLs cannot generally accommodate. As a result, objects at a particular position away from the eye appear in focus, while objects at increasing distances away from that position appear increasingly blurred. Bifocal or multifocal IOLs, which are also generally fixed within the eye, produce two or more foci in order to simulate the accommodation produced by the eye's natural lens. For example, one of the foci may be selected to provide distant vision, while a second focus is selected to provide near vision. While multifocal IOLs improve the ability of a subject to focus on objects over a range of distances, the presence of more than one focus generally results in reduced contrast sensitivity compared to monofocal IOLs.

An IOL may also be used for presbyopic lens exchange. Presbyopia is the condition where the eye exhibits a progressively diminished ability to focus on objects over a range of distances. It is caused by a gradual loss of "accommodation" in the natural lens inside the eye due to age-related changes that make the lens harder and less elastic with the years.

An improvement over the fixed IOLs (either monofocal or multifocal) is an accommodating IOL, or aIOL, which can adjust its power and/or axial position within a particular range. As a result, the patient can clearly focus on objects over a range of distances from the eye in a way that is similar to that provided by the natural lens. This ability to accommodate may be of tremendous benefit for the patient, and more closely approximates the patient's natural vision than monofocal or multifocal IOLs. Such artificial implantable lenses can take the form of injectable IOLs (polymer material injected into the capsular bag), Deformable IOLs (the lens' optic shape change creates optical power change), axially moving IOLs, Dual Optics IOLs, etc, or some combination thereof. Alignment of aIOLs within the eye may be particularly important. Thus, reliable attachment means may be especially useful in assuring quality optical performance for aIOLs.

The human eye contains a structure known as the capsular bag, which surrounds the natural lens. The capsular bag is transparent, and serves to hold the lens. In the natural eye, accommodation is initiated in part by the ciliary muscle and a series of zonular fibers, also known as zonules. The zonules are located in a relatively thick band mostly around the equator of the lens, and impart a largely radial force to the capsular bag that can alter the shape and/or the location of the natural lens and thereby change its effective power and/or focal distance.

In a typical surgery in which the natural lens is removed from the eye, the lens material is typically broken up and vacuumed out of the eye, but the capsular bag is left generally intact. The remaining capsular bag is extremely useful in that it may be used to house an aIOL, which is acted on by the zonules to change shape and/or shift in some manner to affect the lens power and/or the axial location of the image.

The aIOL has an optic, which refracts light that passes through it and forms an image on the retina, and may also include a haptic, which mechanically couples the optic to the capsular bag or holds the aIOL in contact with the capsular bag. During accommodation, the zonules exert a force on the capsular bag, which in turn exerts a force on the optic. The force may be transmitted from the capsular bag directly to the optic, or from the capsular bag through a haptic to the optic. In either case, the lens changes shape and/or position dynamically to keep an object in focus on the retina as its distance from the eye varies.

Desirably, the design of the aIOLs effectively translates the ocular forces of the natural accommodative mechanism of the eye [ciliary muscle—zonules—capsular bag] to maximize accommodation amplitude or range. Also, aIOLs may take into account the problem of lens epithelial cell (LECs) proliferation which can cause opacification and stiffening of the capsular bag over time. This phenomenon is caused by the wound healing reactions of the natural lens epithelial cells that remain on the inside of the capsular bag, often in the narrow ring around the equatorial region. Several methods to prevent the LECs from proliferating have been tried, including removing the LECs as much as possible, mechanically as well as pharmaceutically. Alternatively, design features such as a square edge and spacers have been incorporated into the aIOLs.

As mentioned above, ocular implants may also be used in long-term glaucoma treatment. Glaucoma is a progressive disease of the eye characterized by a gradual increase of intraocular pressure (IOP). This increase in pressure is most commonly caused by stenosis or blockage of the aqueous outflow channel, resulting in excessive buildup of aqueous fluid within the eye. The implant solution typically involves suturing a small plate to the sclera in the anterior segment of the eye at the limbus, and inserting a drainage tube into the anterior chamber of the eye, which may also be secured via a suture to the sclera. Once implanted, the body forms scar tissue around the plate. Aqueous humor flow through the tube causes the tissues above the plate to lift and form a bleb. A bleb is a fluid filled space surrounded by scar tissue, somewhat akin to a blister. The fluid within the bleb then flows through the scar tissue at a rate which desirably regulates IOP. More recently, U.S. Pat. Nos. 5,476,445 and 6,050,970 to Dr. George Baerveldt, et al. disclose glaucoma implants or shunts featuring a flexible plate that attaches to the sclera and a drainage tube positioned for insertion into the anterior chamber of the eye. This type of shunt is sold under the tradename Baerveldt® BG Series of glaucoma implants by Advanced Medical Optics (AMO) of Santa Ana, Calif. The Baerveldt® device has an open tube without flow restricting elements. Temporary sutures are used to restrict fluid flow for a predetermined period, after which the bleb forms and fluid drainage is properly regulated. The temporary sutures are either biodegradable or removed in a separate procedure. This method works well, but the timing of suture dissolution is necessarily inexact, and a second procedure undesirable.

In these and other situations, ocular devices and methods are needed for securely attaching ocular implants in an eye. In some instances, reversal of the attachment means is desirable, for example, to allow the device to be more readily explanted. In addition, there exists a need for an aIOL with increased efficiency in converting an ocular force to a change in power and/or a change in axial location of the image, preferably in a way which also reduces the problem of lens epithelial cell proliferation. There is also a need for an alternative to suturing glaucoma shunts in place.

BRIEF DESCRIPTION OF THE DRAWINGS

Features and advantages of the present invention will become appreciated as the same become better understood with reference to the specification, claims, and appended drawings wherein:

FIGS. 6A and 6B are vertical sectional views through an eye showing the implanted exemplary aIOL of FIGS. 3-5 in two states of accommodation;

DETAILED DESCRIPTION OF THE PREFERRED EMBODIMENTS

Figure 1:
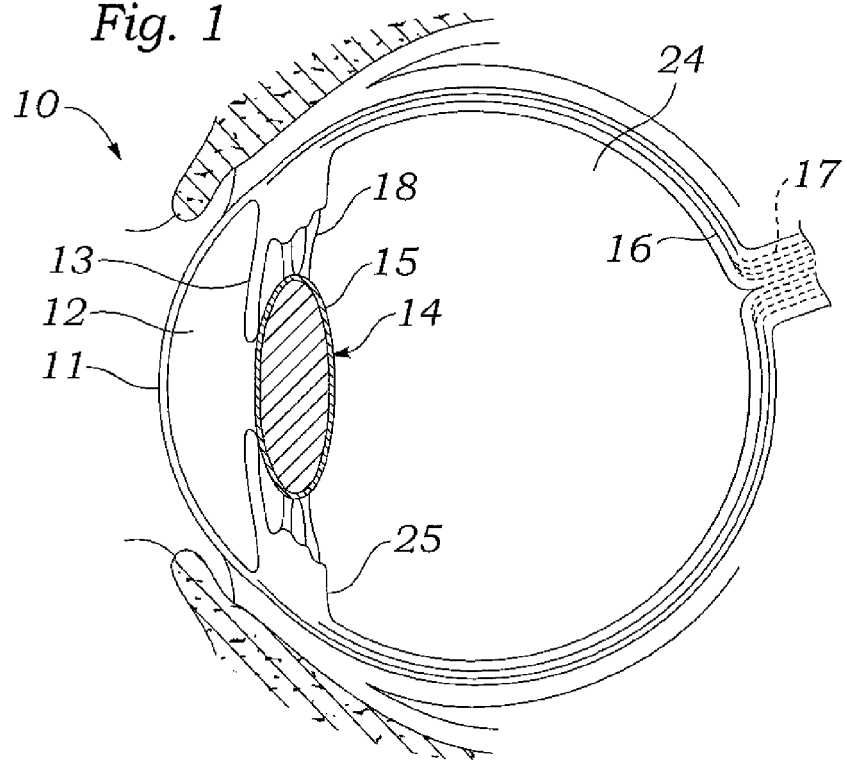
FIG. 1 is a vertical sectional view of a human eye.

Embodiments of the present invention are generally directed to devices, substances, and methods for attaching ophthalmic devices and/or controlling cellular growth after implantation of an ocular device. Embodiments of the present invention are particularly useful when used in conjunction with IOLs. For example, embodiments of the present invention may provide immediate and/or reversible adhesion of an IOL within the capsular bag of an animal or human subject. Surface adherents according to embodiments of the present invention are generally reversible, thus allowing an IOL to be explanted or readjusted subsequent to initial attachment within the eye. While potentially applicable to a variety of ophthalmic devices and IOLs, surface adherents according to embodiments of the present invention may find particular use with accommodating IOLs, which may have attachment and alignment requirements that are especially critical.

In a healthy human eye, the natural lens is housed in a structure known as the capsular bag. The capsular bag is driven by a ciliary muscle and zonular fibers (also known as zonules) in the eye, which can alternately pull on or release on the capsular bag to change its shape. The motions of the capsular bag change the shape of the natural lens in order to change its power and/or the location of the lens, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of shape change, initiated by the capsular bag resiliency, ciliary muscle, and/or zonules, it is desirable that the implanted intraocular lens be configured to utilize the ocular forces produced thereby to change its power and/or location in the eye in a manner similar to that of the natural lens. Such an accommodating lens may produce improved vision over conventional monofocal or multifocal IOLs.

A desirable optic for an accommodating IOL is one that changes shape in response to an ocular force, for example, a squeezing or expanding radial force applied largely to the equator of the optic (e.g., by pushing or pulling on or near the edge of the optic, circumferentially around the optic axis). Under the influence of an ocular force, the optic of the IOL may bulge slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation.

FIG. 1 shows a human eye 10 in vertical section. Light enters from the left of FIG. 1, and passes through the cornea 11, the anterior chamber 12, the iris 13, and enters the capsular bag 14. Prior to surgery, the natural lens occupies essentially the entire interior of the capsular bag 14. After surgery, the capsular bag 14 houses the intraocular lens. The intraocular lens is described in more detail below. After passing through the natural lens, light exits the posterior wall 15 of the capsular bag 14, passes through the posterior chamber 24, and is focused onto the retina 16, which detects the light and converts it to a signal transmitted through the optic nerve 17 to the brain.

Figure 2A:
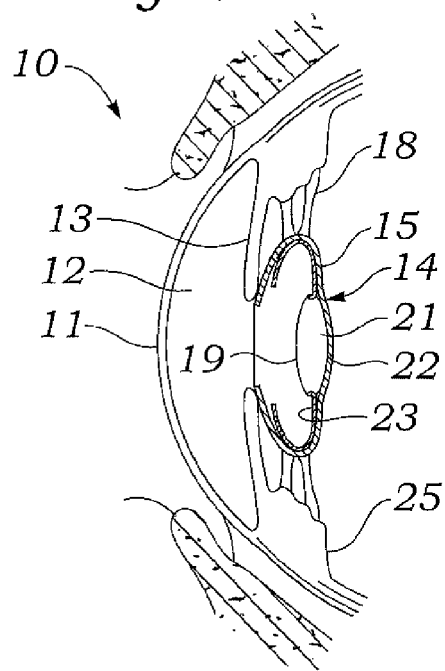
FIG. 2A is a vertical sectional view of a portion of an eye having an implanted intraocular lens, in an accommodative or "near" state.

FIG. 2A shows the eye 10 after an accommodating intraocular lens has been implanted. A well-corrected eye forms an image at the retina 16. If the lens system (cornea+

IOL) has too much or too little power, the image shifts axially along the optical axis away from the retina. The power required to focus on a close or near object is more than the power required to focus on a distant or far object. The difference between the "near" and "far" powers is known typically as the add power or as the range of accommodation. A normal range of accommodation is about 2 to 4 diopters, which is considered sufficient for most patients, but some have a range of about 1 to 8 diopters. As used herein, the term "about" means within plus or minus 0.25 Diopters, when used in reference to an optical power.

The capsular bag is acted upon by the ciliary muscle 25 via the zonules 18, which change the shape of the capsular bag 14 by releasing or stretching it radially in a relatively thick band about its equator. Experimentally, it is found that the ciliary muscle 25 and/or the zonules 18 typically exert a total ocular force of up to about 10 grams of force, which is distributed generally uniformly around the equator of the capsular bag 14. As used herein, the term "about" means within plus or minus 0.5 grams of force, when used in reference to an ocular force. As used herein, an "ocular force" is a force produced by a human or animal eye to provide accommodation, for example, a force produce by the ciliary muscle, zonules, and/or capsular bag of an eye. In human eyes, an ocular force is generally be considered to be a force that is in a range from 0.5 gram force to 20 grams force, 0.5 gram force to 10 grams force, or 0.5 gram force to 6 grams force. Although the range of ocular force may vary from patient to patient, it should be noted that for each patient, the range of accommodation is limited by the total ocular force that can be exerted. It may be desirable that the intraocular lens be configured to vary its power over the full range of accommodation, in response to this limited range of ocular forces. In other words, it is desirable to have a relatively large change in power for a relatively small driving force. As used herein, the term "full range of accommodation" means a variation in optical power of an optic, lens, or lens system that is able to provide both distant and near vision, for example, a change in optical power of at least 3 Diopters or at least 4 Diopters.

Note that the lens may be designed so that its relaxed state (i.e., in the absence of outside forces other than gravity) is a "far" condition for providing far vision (sometimes referred to as "disaccommodative biased"), a "near" condition for providing near vision ("accommodative biased"), or some condition in between the two.

The intraocular lens itself generally has two components, an optic 21, which is made of a transparent, deformable and/or elastic material, and a haptic 23, which holds the optic 21 in place and mechanically transfers forces on the capsular bag 14 to the optic 21. The haptic 23 may have an engagement member with a central recess that is sized to receive the peripheral edge of the optic 21. The haptic and optic may be refractive index matched, though if at least some of the haptic is embedded in or otherwise overlapping the optic the two materials must be index matched.

The lens desirably has a surface adherent thereon, either on just the haptic 23 or also on the optic 21. Various surface adherents are described herein, and any combination and placement of such adherents may be applied to the lens in FIGS. 2A and 2B to facilitate accommodation, as will be described.

When the eye 10 focuses on a relatively close object, as shown in FIG. 2A, the zonules 18 relax and permit the capsular bag 14 to return to its natural shape in which it is relatively thick at its center and has more steeply curved sides. As a result of this action, the power of the lens increases (i.e., one or both of the radii of curvature can decrease, and/or the lens can become thicker, and/or the lens may also move axially), placing the image of the relatively close object at the retina 16. Note that if the lens could not accommodate, the image of the relatively close object would be located behind the retina, and would appear blurred.

Figure 2B:
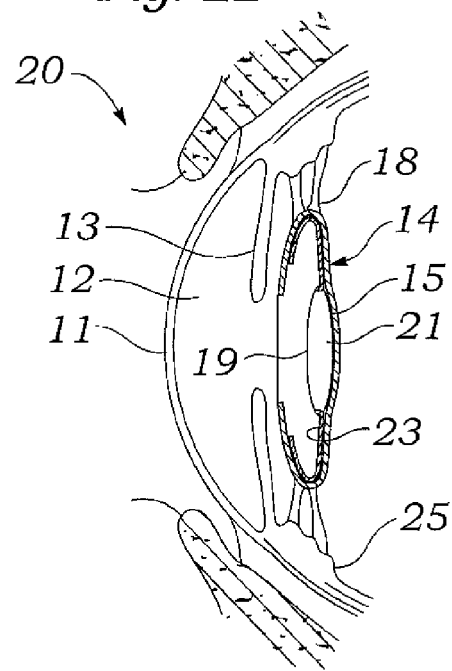
FIG. 2B is a vertical sectional view of the eye of FIG. 2A, in a disaccommodative or "far" state.

FIG. 2B shows a portion of an eye 20 that is focused on a relatively distant object. The cornea 11 and anterior chamber 12 are typically unaffected by accommodation, and are substantially identical to the corresponding elements in FIG. 2A. To focus on the distant object, the ciliary muscle 25 contracts and the zonules 18 retract and change the shape of the capsular bag 14, which becomes thinner at its center and has less steeply curved sides. This reduces the lens power by flattening (i.e., lengthening radii of curvature and/or thinning) the lens, placing the image of the relatively distant object at the retina (not shown).

For both the "near" case of FIG. 2A and the "far" case of FIG. 2B, the intraocular lens itself changes shape in response to ocular forces provided by the ciliary muscles and/or the capsular bag. For a "near" object, the haptic 23 compresses the optic 21 at its edge, increasing the thickness of the optic 21 at its center and increasing the curvature of at least a portion of its anterior face 19 and/or its posterior face 15. As a result, the power of the optic 21 increases. For the "far" object, the haptic 30 expands, pulling on the optic 21 at its edge, and thereby decreasing the thickness of the optic 21 at its center and decreasing the curvature of at least a portion of its anterior face 19 and/or its posterior face 15. As a result, the lens power decreases.

Note that the specific degrees of change in curvature of the anterior and posterior faces may depend on the nominal curvatures. Although the optic 21 is drawn as bi-convex, it may also be plano-convex, meniscus or other lens shapes. In all of these cases, the optic is compressed or expanded by forces applied by the haptic to the edge and/or faces of the optic. In addition, there may be some axial movement of the optic. In some embodiments, the haptic is configured to transfer the generally symmetric radial forces symmetrically to the optic to change the shape or surface curvature of the optic in an axisymmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optic may optionally have one or more diffractive elements, one or more multifocal elements, and/or one or more aspheric elements.

Certain exemplary embodiments herein provide a haptic partly embedded within an adjustable or accommodative central optic. The haptic transmits forces to alter at least one of the shape and the thickness of the adjustable optic. The materials of the haptic and optic may have similar compressive or spring moduli, to encourage direct transfer of forces and reduce uneven expansion/contraction and accompanying tension therebetween, though the haptics are generally somewhat stiffer to be capable of transmitting capsular forces. Additionally, similar material stiffness may reduce the mismatch in shrinkage rates during molding or post-processing, which mismatch may ultimately negatively impact lens optical resolution. In one embodiment, the haptic is stiffer than the optic. Moreover, the two materials have the same or similar refractive indices to reduce any unwanted glare or reflection from light passing across adjacent surfaces. A number of such embedded optics may be seen in U.S. Patent Publications 2008-0161913 and 2008-0161914, the disclosures of which are expressly incorporated by reference herein.

A number of intraocular lenses may be adapted to the concepts described herein to improve the accommodative performance of the haptic or IOL, such that compressive/tensile forces may be more efficiently transferred from the haptic to the optic. It should be understood that any combination of individual haptic or IOL features described herein, where appropriate, may be formed even if not explicitly described or shown. It should also be noted that while described in relation to aIOLs, surface adherents according to embodiments of the present invention may be used with a variety of types of IOLs or other ophthalmic devices (e.g., shunts). For instance, any monofocal or multifocal IOL may benefit from a surface adherent on its haptic and/or optic to fix the lens in position, enhance stability, and/or prevent PCO. For example, a thermo-reversible adhesive, which solidifies at body temperature, may be useful to initially attach an IOL and subsequently reverse the attachment temporarily to readjust the IOL position by flowing a cold BSS solution through the eye. Likewise, both phakic IOLs (PIOL) may be adapted with the surface adherents described herein. For instance, a phakic anterior chamber IOL may have microfibers on its haptics for better fixation.

Figure 3:
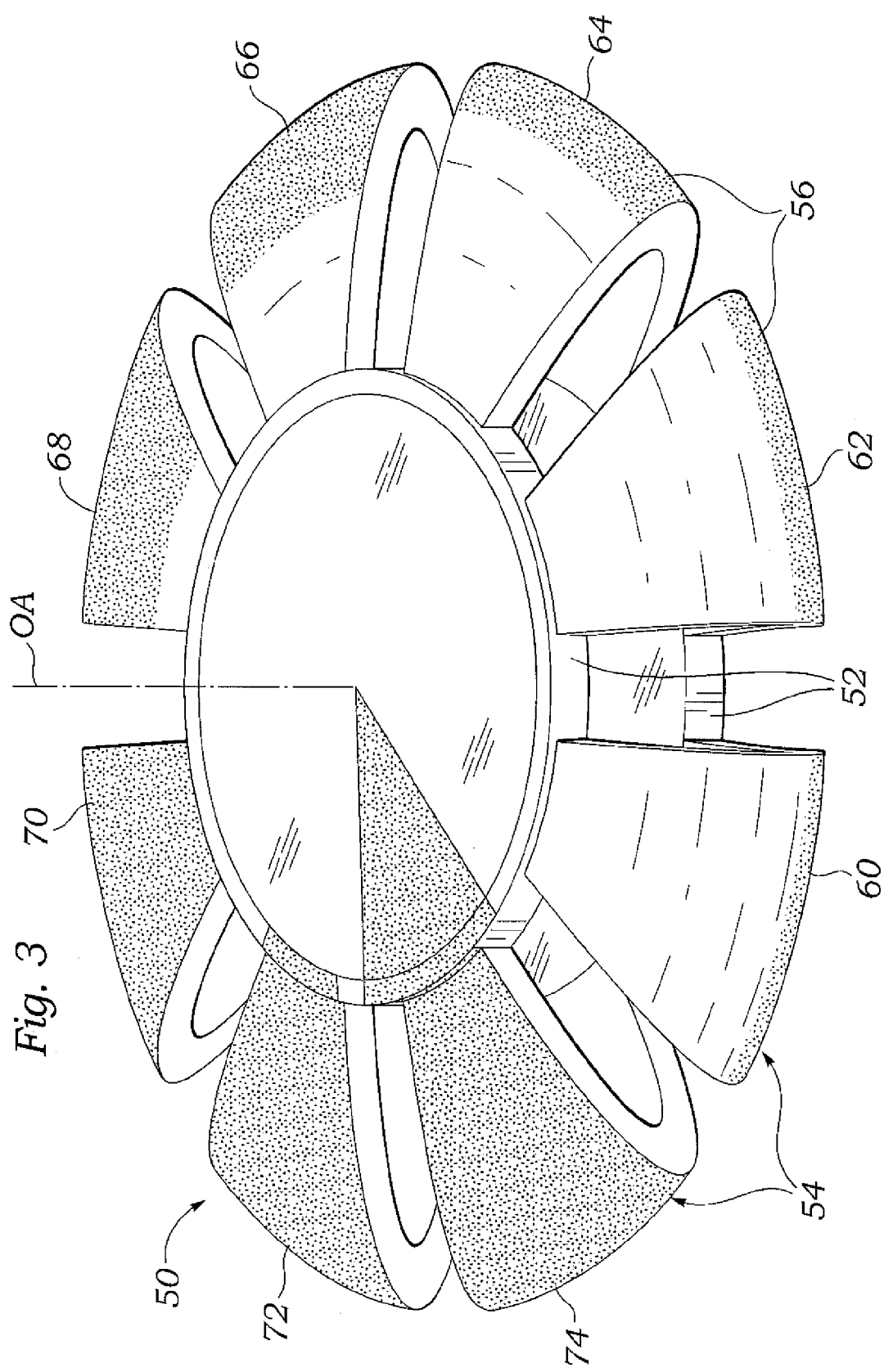
FIG. 3 is a perspective view of an intraocular lens having a pair of axially spaced-apart and centered optics, and a plurality of convex haptic legs connecting the optics and radiating outward therefrom.

FIG. 3 is a perspective view of an accommodative IOL 50 having a pair of axially spaced-apart optics 52 centered on an optical axis OA, and a plurality of convex haptic legs 54 connect the optics and radiating outward therefrom. The haptic legs 54 are configured to transmit forces from the surrounding capsular bag/zonules to alter the spacing between the optics 52.

In some embodiments, the aIOL 50 is symmetric across a midplane perpendicular to the optical axis OA such that there are matching legs 54 connected to each optic 52. Preferably, each pair of matching legs 54 joins together at their outer ends in a convex outer curve 56 that may be configured to generally match the shape of a capsular bag of an eye into which the intraocular lens is inserted. As illustrated, there may be eight pairs of matching legs 54, though more and as few as three are contemplated. The convex outer ends of the haptic legs 54 provides a capsular bag-filling outer profile to the aIOL 50 that effectively couples the bag forces to the dual optics 52 to either axially expand or contract the spacing therebetween. That is, forces exerted on the outer ends of the haptic legs 54 are transmitted through the legs to cause the spaced optics 52 to move apart or toward each other, thus changing the dual lens focal length. Although movement between the two optics 52 may be configured to amplify a change in power (accommodative range), in some embodiments the aIOL 50 includes only one of the lenses 52, for example, to reduce criticality of alignment of the aIOL within the eye.

Figure 4:
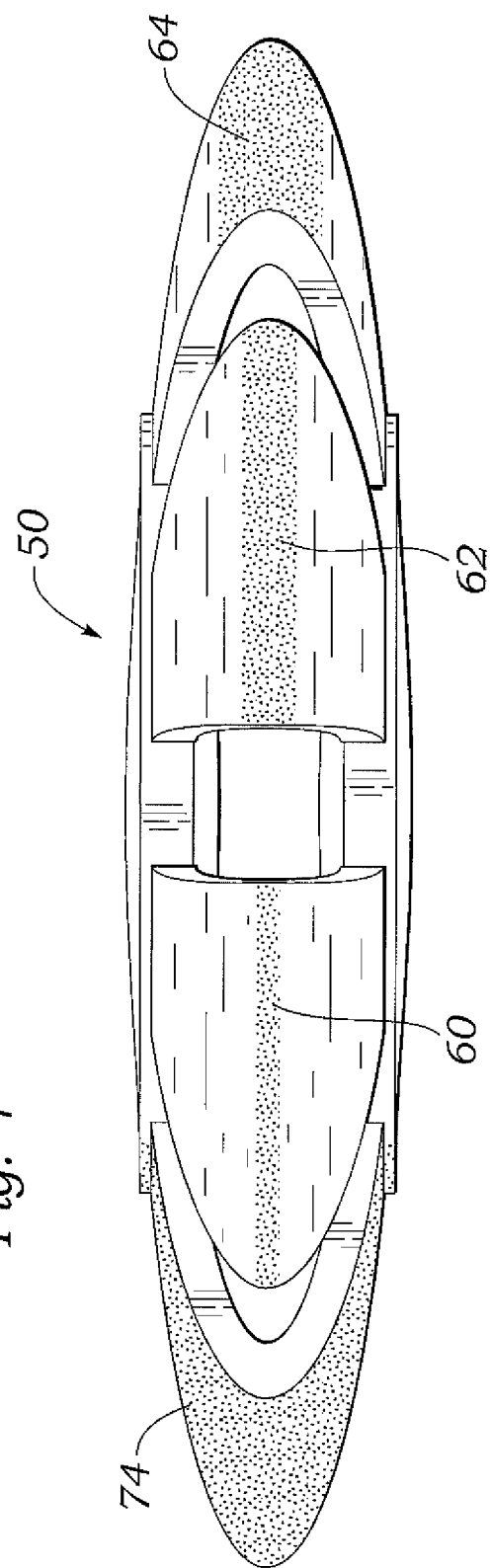
FIG. 4 is an elevational view of the intraocular lens of FIG. 3.

In accordance with the principles described herein, varying degrees of a surface adherent may be provided to the exterior of the aIOL 50. As seen in FIGS. 3 and 4, gradually larger regions of stippling are shown around the aIOL 50 and on succeeding haptic legs 54. A thin band of stippling 60 is shown on a leg 54 at the lower left in FIG. 3, with gradually larger regions of stippling shown at 62-70 in a CCW direction around the aIOL 50. The largest region of stippling in this series at 70 covers the entire haptic leg 54. Continuing CCW, two other regions of stippling 72, 74 extend partway and all the way radially inward onto sectors on the optics 52 (the lower half shall be considered to be symmetric with the upper half, though such is not strictly necessary).

The regions of stippling 60-74 represent application locations for a number of different potential surface adherents according to embodiments of the present invention. In general, surface adherents according to embodiments of the present invention are advantageously provide adhesion within a relatively short period of time (e.g., less than or equal to one second, less than 1 to 5 minutes, or less than 1 to 5 hours), help to prevent or control cell growth (e.g., PCO), are reversible, and/or otherwise provide mechanism for easily detaching a device after adhesion to a part of an eye. For instance, the regions of stippling 60-74 could be a thermo-reversible bioadhesive polymer such as polymerized N-isopropyl acrylamide (pNIPAM) (also known as NIPAAm (poly (N-isopropylacrylamide)). Alternatively, the regions of stippling 60-74 could comprise a plurality of microfibers, for example, having physical surface texturing designed to mimic the feet of certain lizards and insects. Each of these alternatives will be discussed in more detail below, including their preferred sites of application on the aIOL. Preferably, the amount of surface adherent is sufficient to hold the aIOL in place under normal ocular forces after insertion into an eye. In some embodiments, reversible adhesion is provided by a substance that changes its adhesion characteristic with an intensity or wavelength of light, vibration of the adhesion interface, application or concentration of a chemical substance, exposure or intensity of an electric or magnetic field, or the like.

Polymeric systems that may modify adhesive properties in response to changes in the physical and chemical characteristics of the physiological medium are promising candidates to achieve reversible tissue adhesion. Several groups have explored the use of dynamic stimulus-responsive surface chemistries for cell patterning, thermo-active, electrical-active, and photo-active chemistries have been defined for cellular adhesion. In general, all of these chemistries operate under the same principle. These substances can be switched from a state that prevents cellular attachment to a state that promotes it. In the context of the present application, a reversible adhesive means one which can change state depending on certain stimulus, such as temperature for a thermo-reversible adhesive. Other possible stimuli include mechanical (e.g., vibration), light, radiation, chemical, or others.

A particularly useful composition for use in the present invention is a thermo-reversible bioadhesive polymer, such as a composition which is liquid at or below room temperature and forms a high viscosity layer or gel at body temperature.

Polymers having bioadhesive properties are for instance water-soluble cellulose derivatives, such as sodium carboxymethyl cellulose, and polyacrylic acids, which are used in many pharmaceutical preparations to improve the contact between drug and body. Improved uptake of ophthalmic drugs has been achieved by using vehicles containing viscosity-increasing polymers such as the cellulose derivatives, polyvinyl alcohol and polyvinylpyrrolidone. Thermogelling pharmaceutical preparations are described in U.S. Pat. Nos. 4,478,822, 4,474,751, 4,474,752 and 4,474,753, which refer to a drug delivery system which at room temperature has the properties of a liquid, but forms a semi-solid gel at human body temperatures. The compositions to be administered comprise 10 to 50% by weight of a polymer, which is a tetra-substituted derivative of certain diamines containing approximately 40 to 80% poly(oxyethylene) and approximately 20 to 60% poly(oxypropylene), as a drug delivery vehicle. In this system the gel transition temperature and/or the rigidity of the gel can be modified by adjustment of the pH. Other systems are known in which the gelling is induced by an increase in the amount of electrolytes or a change in pH. Further, certain water-soluble nonionic cellulose ethers in combination with a charged surfactant and optional additives in water have the property of being liquid at room temperature and forming a gel when warmed to body temperature, and the process is reversible.

An ideal thermo-reversible bioadhesive polymer for intraocular use should be nontoxic and biocompatible. Polymerized N-isopropyl acrylamide (pNIPAM) has been shown not to be toxic to neural tissue and is commonly used in cell and tissue cultures for its reversible cell adhesion properties. Previous reports showed that cells may be attached and detached from pNIPAM coated culture dishes without exhibiting any changes in morphology. Some studies show that pNIPAM has a lower critical solution temperature of 31° C. in an aqueous environment. This may indicate that the reversible thermoresponsive adhesive or hydrogel (pNIPAM) exhibits decreased solubility or swelling in water as the temperature is increased, due to a phase transformation at the lower critical solution temperature. Thus, pNIPAM may be switched from a state that promotes cellular attachment to a state that prevents cellular attachment, as the temperature of the surface is decreased. A particular characteristic of this material is the ability to be adhesive at body temperature (37 C) and not adhesive at room temperature. Various applications for such a bioadhesive are disclosed in US Patent Publication No. 2008-0140192, assigned to the University of Southern California, which is expressly incorporated herein by reference.

The use of this type of thermo-reversible, or some other type of reversible, bioadhesive polymer with accommodating IOLs (aIOLs) may resolve two key issues currently challenging the use of aIOLs technologies (that is, prevention of LECs from proliferating ("PCO") and optimization of the coupling of the capsular bag to the aIOLs) by fully adhering the aIOL to the capsular bag once the aIOL is in place. Further, cold or room temperature saline could be injected at the device and/or into the capsular bag to release the adhesive to allow for re-position of the aIOL or its explantation.

If applied to a lens of an IOL or aIOL, the lens could be coated with the thermo-reversible bioadhesive polymer. In this case, the lens could be handled in a manner consistent with current standard cataract surgical procedures and inserted at operating room temperatures. Once the lens is implanted in the eye, the thermo-reversible polymer (such as pNIPAM) properties will allow the IOL to adhere to the capsular bag. The coating can be selective (specific areas of the aIOL) or on all surfaces of the aIOL as required by the aIOL design to prevent LECs proliferation and to optimize capsular bag coupling. Also, as mentioned above, the adhesive may be reversible based on some other stimulus than a temperature change.

In a preferred embodiment, a thermo-reversible bioadhesive polymer is coated on the exterior of the aIOL 50 prior to implant, and remains in a state that prevents cellular attachment (less adherent) while outside the body. After implant into the capsular bag, and a rise in temperature to match the body's, the thermo-reversible bioadhesive polymer undergoes a change of state to one that that promotes cellular attachment (more adherent). Postsurgically, should the aIOL 50 require removal, replacement, or re-positioning, a cold saline or other such solution may be used to cause the thermo-reversible bioadhesive polymer to revert back to its less adherent state. Preferably, the amount of thermo-reversible bioadhesive polymer is sufficient to hold the aIOL 50 in place under normal ocular forces after insertion into an eye.

With reference to FIGS. 3 and 4, one or more of the varying sizes shown of the stippled regions 60-74 may be reproduced on all haptic legs 54 of the aIOL 50. In a preferred embodiment, the surface adherent is provided in thin bands, as in the small band 60, on the outer end of each haptic leg 54. One benefit from providing the thin surface adherent bands 60 is that the equatorial region of the haptic legs 54 adheres better within the area of the capsular bag where the zonular fibers attach to the bag. Also, providing adhesive between the haptic legs 54 and the capsular bag may prevent cell migration over these contact areas. Lens epithelial cell (LECs) often remain in the tight equatorial corner inside the capsular bag after attempts at removal. Adhering the haptic legs 54 to the capsular bag in these areas effectively eliminates any gap therebetween and thus inhibits further overgrowth. In some embodiments, a surface adherent is applied to selectively provide adhesion in a region where the zonules attach to the capsular bag, for example, to provide enhanced transfer of ocular forces to the capsular bag and aIOL. In such embodiments, other surface portions of the haptic and/or optic may be free of the bioadhesive polymer, for example, to allow relative motion between the capsular bag and the aIOL.

Alternatively, larger bands of a surface adherent as the band 62 may be used, or even larger bands as seen at 64-68, moving CCW around the aIOL 50. Ultimately, the entirety of each haptic leg 54 may be covered with the surface adherent, as seen at 70.

Depending on the effect on the optical performance, surface adherent may also cover a portion or all of the external surface of the optics 52 (or just one of the optics). For instance, region 72 shows the surface adherent extending inward beyond the corresponding haptic leg 54 and onto the outer rim of the optic 52. Likewise, region 74 shows the surface adherent extending inward beyond the corresponding haptic leg 54, over the outer rim of the optic 52, and onto the surface of the optic to its center. The stippling 74 has been drawn to indicate that if all of the sectors were so configured that the entire exterior surface of the aIOL 50—that is, both the optics 52 and the haptic legs 54—would be covered with a surface adherent. In some embodiments, a surface adherent is located on at least portions of one or both optics 52, but no, or little, surface adherent is located on the haptics legs 54, for example, to hold the aIOL in place and allow relative motion between the capsular bag and haptic legs 54.

As mentioned above, the regions of stippling 60-74 could be physical surface texturing designed to mimic the feet of certain lizards and insects. The ability of geckos, spiders and flies to adhere to seemingly shear surfaces has long fascinated researchers. For instance, geckos' exhibit a remarkable ability to stick to surfaces without the use of an adhesive substance (such as a polymer, etc.). Geckos foot surfaces are characterized by a plurality of microfibers that in some aspects are similar to synthetic microfibers. The adherent principle (i.e., adhesion through physical surface structure rather than exuded polymers, or other similar contact adhesives, etc.) is believed to be due to van der Waals forces.

A van der Waals force is the attractive or repulsive force between molecules (or between parts of the same molecule) other than those due to covalent bonds or to the electrostatic interaction of ions with one another or with neutral molecules. The term includes permanent dipole-permanent dipole forces, induced dipole-induced dipole forces, and instantaneous induced dipole-induced dipole (London dispersion forces). It is also sometimes used loosely as a synonym for the totality of intermolecular forces. Van der Waals forces are relatively weak compared to normal chemical bonds.

Through various molding processes and techniques, it is possible to mimic the microfiber structure found on gecko feet that provides such an adherent surface. Consequently, one "surface adherent" as defined herein is a surface having a plurality of microfibers thereon. Microfibers, in this context, will be defined as fibers having a diameter of between 3-5 microns (micrometers, µm). The microfibers will be provided in sufficient numbers/density over a particular area of the aIOL to provide adhesion between the aIOL and the surrounding capsular bag. This would provide immediate IOL-to-capsular bag fixation after implant as well as an easy detachment process through pealing. Preferably, the microfibers will be provided in sufficient numbers/density over a sufficient area so as to hold the aIOL 50 in place under normal ocular forces after insertion into an eye.

For instance, microfibers may be molded in sufficient quantities along the perimeter of the haptic (such as in the thin bands 60, 62, or 64 in FIGS. 3 and 4) so that the existing capsular bag could adhere to them. Again, this adhesion will allow the haptic legs 54 to be more effectively pulled bringing the two optics closer (during dis-accommodation, reducing power) and pushed forcing the optics apart (during accommodation, increasing power). Locating these fibers primarily along the equator of the haptic legs 54 within the band where the zonular fibers attach to the bag provides excellent results in terms of improved force transfer during accommodation. Proper shape and sizing of the haptic structure would be necessary, as described below.

An exemplary discussion of a variety of microfiber configurations is given in U.S. Pat. No. 7,344,617 to Dubrow, the content of which is expressly incorporated herein.

Different embodiments of the invention comprise a range of densities (e.g., number of microfibers per unit area of a substrate to which microfibers are attached or associated). The number of microfibers per unit area can optionally range from about 1 microfiber per 10 micron$^2$ up to about 200 or more microfibers per micron$^2$; from about 1 microfiber per micron$^2$ up to about 150 or more microfibers per micron$^2$; from about 10 microfibers per micron$^2$ up to about 100 or more microfibers per micron$^2$; or from about 25 microfibers per micron$^2$ up to about 75 or more microfibers per micron$^2$. In yet other embodiments, the density can optionally range from about 1 to 3 microfibers per square micron to up to approximately 2,500 or more microfibers per square micron.

In terms of individual fiber dimensions, it will be appreciated that by increasing the thickness or diameter of each individual fiber, one will again, automatically increase the area of the fiber that is able to make intimate contact with another surface, whether such contact is with a fiber that is directly orthogonal to the second surface or is parallel or tangential with that other surface. Preferred fiber thicknesses are optionally between from about 3-5 microns. Choice of microfiber thickness can also be influenced by compliance of such microfibers (e.g., taking into account that microfiber's composition, etc.). Thus, since some compositions can produce a less compliant microfiber at greater diameter such changes can optionally influence the choice of microfiber diameter.

In the case of parallel or tangential contact between fibers from one surface and a second surface, it will be appreciated that by providing fibers of varying lengths, one can enhance the amount of contact between a fiber, e.g., on an edge, and the second surface, thereby increasing adhesion. Of course, it will also be understood that for some fiber materials, increasing length may yield increasing fragility. Accordingly, preferred fiber lengths will typically be between about 30 microns or less up to about 130 microns.

Figure 5:
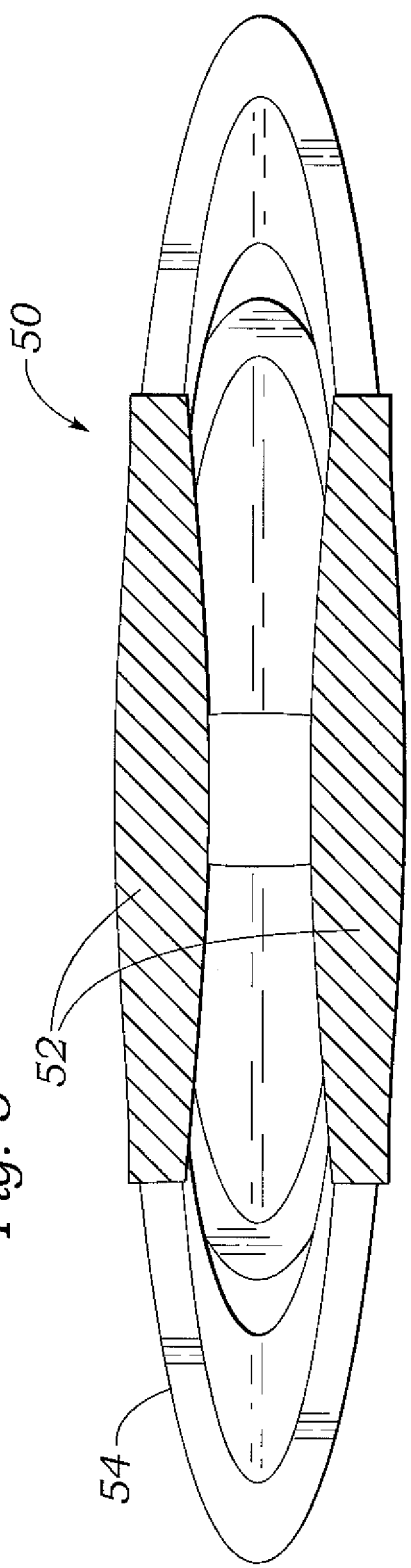
FIG. 5 is a sectional view of the intraocular lens of FIG. 3.

In terms of the aIOL 50 illustrated in FIGS. 3-5, the microfibers mimicking gecko feet are desirably provided only on the haptic legs 54, and not on the optics 52, as the physical surface irregularities thus presented may interfere with the optical transmission quality. However, as with other surface roughening treatments, microfibers may be provided on an outer portion of the optics 52 without deterioration of vision, such as in regions like 72 around the aIOL 50.

It is also possible to combine different surface adherents on a single lens, such as a bioadhesive (e.g., pNIPAM) and microfibers (e.g., gecko feet). For example, microfibers may be provided on the IOL haptics, while a bioadhesive is coated on at least a portion of the optic for lower interference with the optical transmission through the lens. One contemplated embodiment is for microfibers on the IOL haptics to be coated with a bioadhesive which is reversible so as to be relatively thick at room temperature and liquid at body temperature. This configuration prevents the microfibers from sticking to surrounding structures and instruments prior to implant, but exposes the microfibers after implant for good adherence to the capsular bag.

FIGS. 6A and 6B are vertical sectional views through an eye showing the implanted exemplary aIOL of FIGS. 3-5 in two states of accommodation. In FIG. 6A the zonules pull on the equatorial region of the capsular bag and cause elongation of the aIOL 50, such that the two optics 52 are brought closer together, thus decreasing the optic power. In FIG. 6B the zonules push radially inward on the equatorial region of the capsular bag and cause a squeezing of the aIOL 50', such that the two optics 52 are separated in the axial direction, producing an increase in the power of the optic. Again, these reactions to the muscle movement of the zonules are accentuated by the intimate and adherent contact between at least the equatorial region of the exemplary aIOL haptics with the capsular bag.

Figure 7:
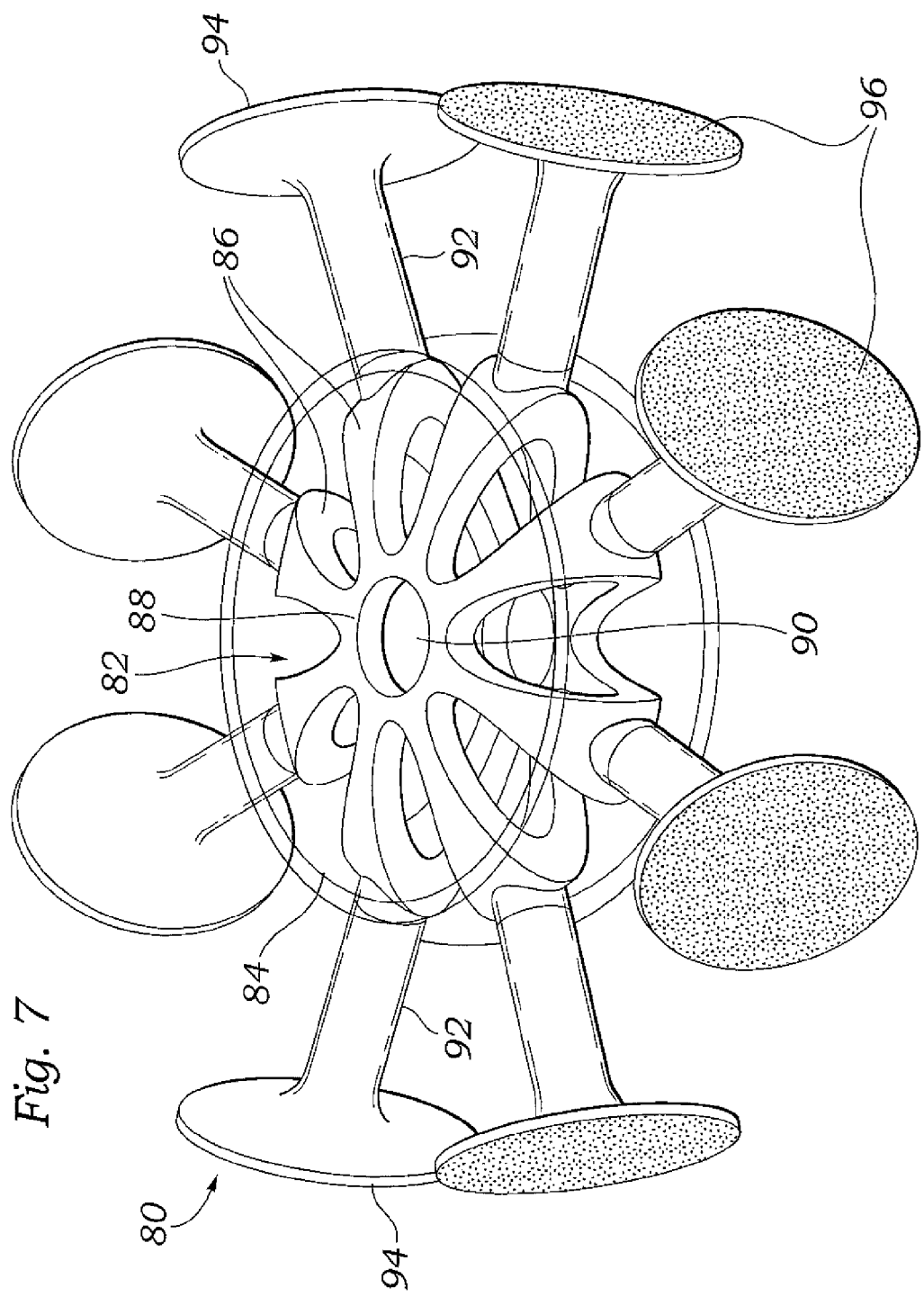
FIG. 7 is a perspective view of an intraocular lens having an optic within which is embedded a portion of an accommodative haptic, the accommodative haptic including a central vaulted portion, a plurality of spokes each having a unitary outer end, axially spaced apart bifurcated inner ends connected in two axially spaced planes, and central throughholes in the central vaulted portion.

Another embodiment of aIOL 80 into which the benefits of the present application may be incorporated is shown in FIG. 7. The aIOL 80 includes a haptic 82 embedded within a relatively softer optic 84. As was described in U.S. Patent Publications 2008-0161913 and 2008-0161914, mentioned above, various aIOL embodiments provide a haptic partly embedded within an adjustable or accommodative central optic. The haptic transmits forces to alter at least one of the shape and the thickness of the adjustable optic. The materials of the haptic 82 and optic 84 have similar refractive indices to reduce any unwanted glare or reflection from light passing across adjacent surfaces.

The haptic 82 includes a plurality of spoke-like legs 86 that each terminate at an outer end in a convex surface and include bifurcated segments that converge in two axially-spaced inner rings 88 surrounding central apertures 90. The resulting structure is a series of vaulted legs 86 joined in the middle. Each leg 86 further includes a cylindrical strut 92 extending outward from its outer end that ends in an enlarged disk-shaped head 94. Each strut 92 and head 94 combination resembles a combustion engine cylinder valve.

The outermost face of each head 94 has a surface adherent 96 thereon, indicated by stippling. Although the entire outer face of each head 94 is shown covered with the surface adherent 96, only portions thereof may be covered, such as, for instance, the peripheral edge. The aIOL 80 of FIG. 7 relies on the same capsular bag fixation technique as described above, with adhesion along the capsular bag equator to push and pull on the single optic 84. In this case, instead of relying on power change from dual optic movement, the forces are transferred via the haptic 82 towards the center of the soft optic body 84, thus inducing power by changing the shape or curvature of the optic surface. In one version, each head 94 has an oval shape and is formed of a material and thickness that easily conforms to the existing capsular bag geometry once placed in the eye.

Various configuration of surface adherent 96 are contemplated for the aIOL 80, including an adhesive such as the thermo-reversible bioadhesive polymer described above, or microfibers. In the case of microfibers, the fibers would desirably be formed normal to the oval-shaped haptic heads 94.

It should be understood that the aIOL embodiments of FIGS. 3 and 7 are only two of a myriad of lens designs that could benefit from direct attachment to the capsular bag using the surface adherents described herein. Again, the principle attachment area would at least be along the equator of the capsular bag, though other designs may benefit from anterior or posterior capsular bag attachments as well.

Figure 8B:
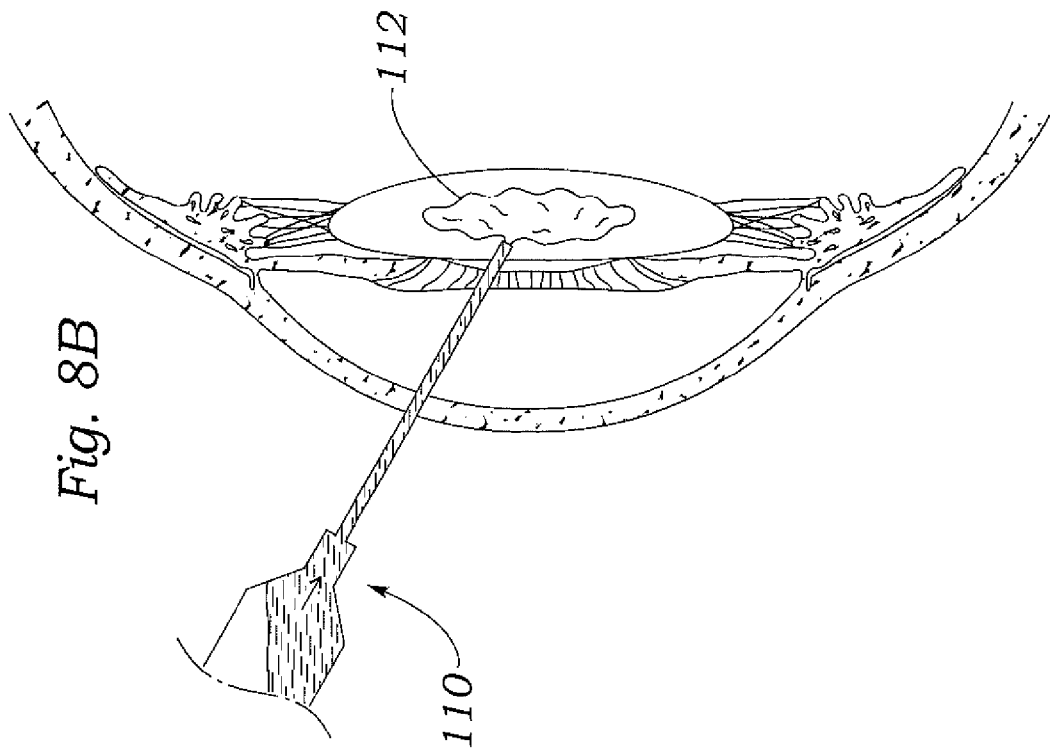
FIG. 8B is a vertical sectional view through an eye showing introduction of an injectable polymer aIOL into the capsular bag prepared as in FIG. 8A.
Figure 8A:
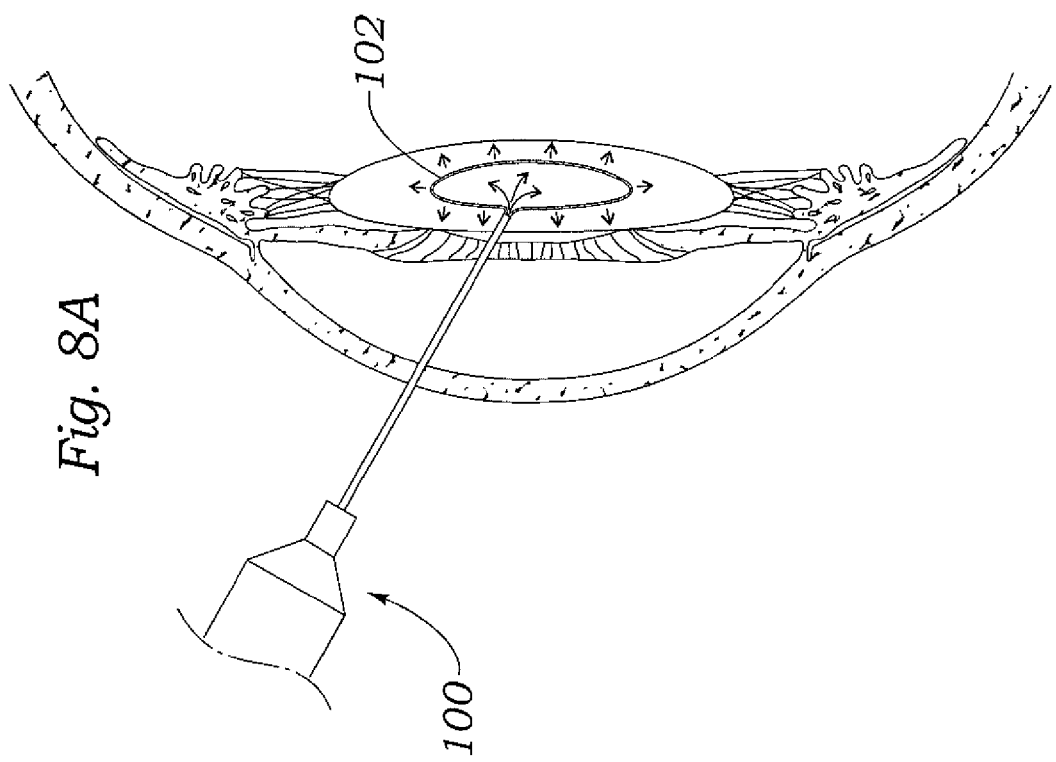
FIG. 8A is a vertical sectional view through an eye showing preparation of the inner surface of the capsular bag by application of a bio-adhesive.

FIGS. 8A and 8B show a modified technique for implanting an injectable polymer aIOL in accordance with the principles described herein. Injectable aIOLs are known in the art, such as in U.S. Pat. Nos. 4,542,542, 4,608,050, 6,589,550, 6,598,606, and 7182780, the aggregate disclosures of which are expressly incorporated by reference herein. In general, these patents describe techniques for removing a cataracteous and/or presbyopic natural lens from the capsular bag of the eye and replacing it by a lens-forming liquid material injected directly into the capsular bag. The liquid material is a partially polymerized material, which can undergo a curing process in the eye and thereby form a solid lens implant. The lens implant acts as a substitute for the natural lens and aims to substantially restore the features of the natural lens of the young eye. The defective natural lens matrix can be removed by a conventional surgical method involving an ultrasound probe, such as a phacoemulsification method involving aspiration. In order to facilitate the removal of the lens matrix and refilling with lens forming liquid material, a capsulotomy, i.e. a capsulorhexis, is prepared from a circular or essentially circular capsulotomy in the capsular bag wall, typically with a diameter of from about 0.5 to about 2.5 mm. An injection syringe needle is inserted through an incision in the eye and through the capsulorhexis into the capsular bag so the lens-forming liquid material can be injected into the capsular bag.

A preferred technique is to "coat" the capsular bag with a layer of the thermo-reversible polymer just prior to the aIOL implantation/capsular bag filling with polymer material injected into it (for Injectable IOLs) during the cataract surgery procedure. This can be achieved for example by manually applying the thermo-reversible polymer by the surgeon using adjunct instrumentation, by implanting a temporary IOL, device or "bag-filling balloon" that will transfer the layer to the capsular bag and then be removed. Once again, a reversible adhesive in general may be used, the thermo-reversible polymer being particularly useful.

For instance, FIG. 8A illustrates a cannula 100 inserted into the previously evacuated capsular bag space and inflating a balloon 102. The balloon 102 has been coated with a preferred bioadhesive, such as pNIPAM as described above. Eventually, the balloon 102 fills the space within the capsular bag and the adhesive transfers to the bag. The balloon 102 is then deflated and the cannula 100 removed.

Subsequently, the surgeon advances the needle of a syringe 110 into the capsular bag and injects a polymer material 112 that will form the aIOL. The material 112 fills the space within the capsular bag and comes into intimate contact with the adhesive previously applied. This arrangement fully adheres the aIOL to the capsular bag and will effectively couple the forces of the natural accommodative mechanism of the eye to the aIOL to maximize accommodation amplitude for years with no expected degradation over time. Full adhesion of the aIOL/Injectable Polymer to the capsular bag will also prevent lens epithelial cell (LECs) migration over those areas.

Rather than injecting an amorphous mass into the capsular bag, an injectable IOL could be encapsulated within a flexible structure like a balloon which is then inflated to fill the capsular bag. Such a configuration may be better received by the immune system of the eye. In such a case, an adhesive layer may be provided on the outside of balloon rather than on the inside of the capsular bag. The balloon could be partly inflated prior to implant or fully inflated after implant, though obviously the latter reduces the size of the capsulotomy necessary.

Figure 9:
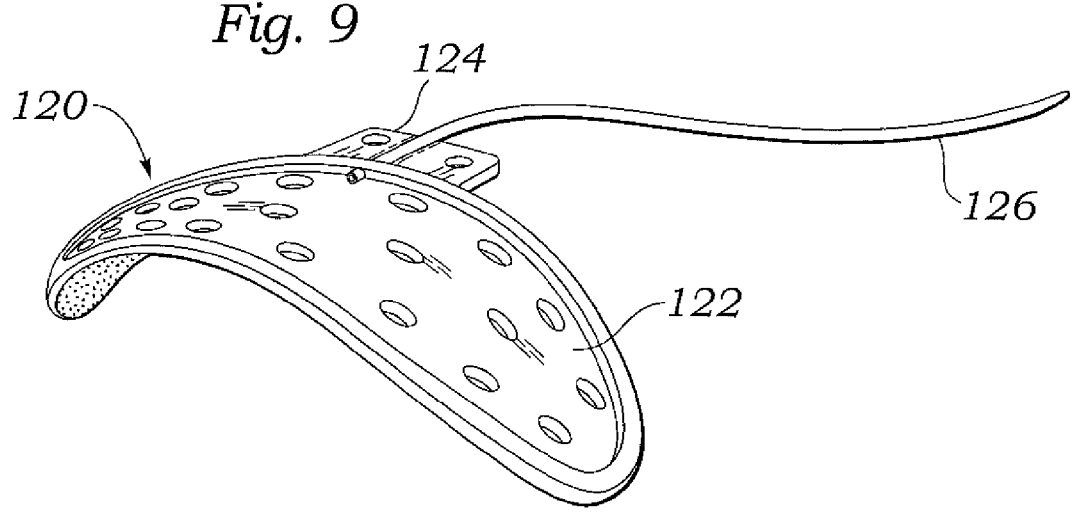
FIG. 9 is a perspective view of an exemplary glaucoma shunt that may be fixed in place using the principles described herein.
Figure 10:
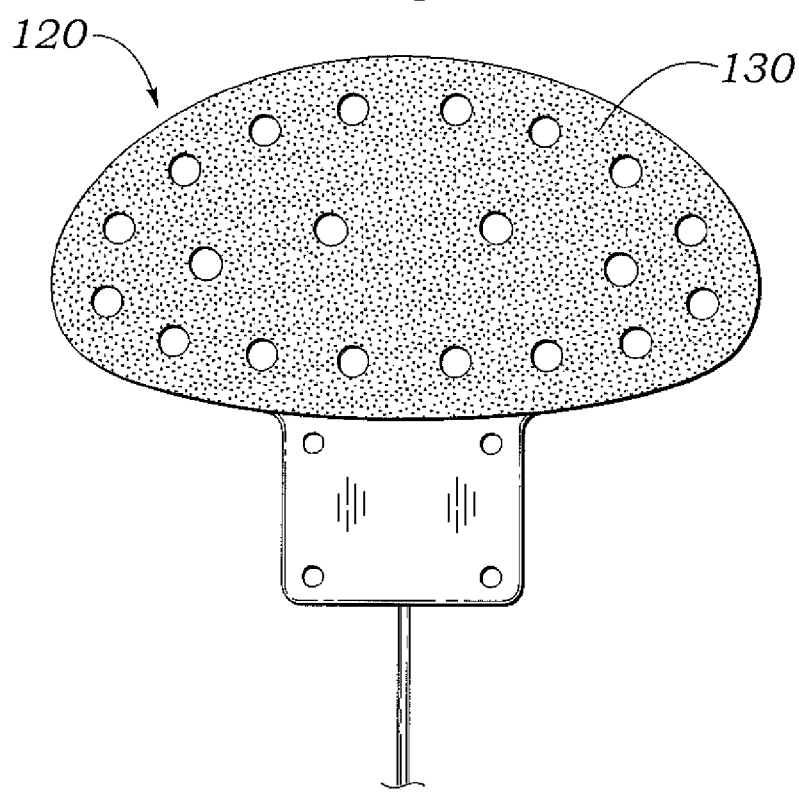
FIG. 10 is a bottom plan view of the glaucoma shunt of FIG. 9 showing an exemplary distribution of an adhering surface.

Another use for the surface adherents described herein is with glaucoma shunts, such as shown at 120 in FIGS. 9 and 10. The shunt 120 includes a large curved plate 122 that will conform around the sclera and typically has a small tab 124 extending from one side. An elongated flexible drainage tube 126 opens at one end over the plate 122, and another end is free. The free end will be inserted into the inner fluid chamber of the eye to initiate fluid drainage therefrom.

The underside of the plate 122 preferably is covered with a surface adherent, shown as stippling in FIG. 10. Again, the entire surface may be covered, or at least those portions in between fenestration holes. Alternatively, only a peripheral edge or some other portion of the plate underside may be covered. In any event, the surface adherent will bond to the sclera, thus eliminating the need for temporary sutures, and perhaps also the need for the tab 124 that typically was used for a suture anchor. A preferred surface adherent for the glaucoma shunt 120 is microfibers as described above.

In addition to securing IOLs in the eye, such as in the capsular bag, certain of the adhesives described herein are suitable for other ophthalmic uses. For instance, as described previously the procedure for injecting polymer type of IOL requires formation of an essentially circular capsulotomy in the capsular bag wall, typically with a diameter of from about 0.5 to about 2.5 mm. One application of the reversible adhesives described herein is in plugging this capsulorhexis. A small amount of pNIPAM, for example, deposited into the capsulorhexis may be sufficient to close it. The instrument that deposits the adhesive may include some form of shaper that spreads the adhesive in a thin layer across the capsulorhexis, and may linger for a sufficient time for a thermo-responsive adhesive to set up. Alternatively, a light-sensitive adhesive may be used which sets up on absorbing light from an LED or other such source.

Another potential application for the adhesives described herein is in fixing capsular bag ruptures after implant of an IOL, PIOL or aIOL. Again, an adhesive responsive to an external stimulus such as a temperature change may be deposited at a tear in the capsular bag and held in place long enough to gel or otherwise harden.

Still another application is in repair of at least small tears between the zonules and the capsular bag.

Finally, the adhesives may be used to seal a surgical incision through the cornea/sclera after cataract surgery.

While the invention has been described in its preferred embodiments, it is to be understood that the words which have been used are words of description and not of limitation. Therefore, changes may be made within the appended claims without departing from the true scope of the invention.

What is claimed is:

1. An accommodating intraocular lens (aIOL) for implantation into a capsular bag of an eye, comprising:
   an adjustable optic having an axial thickness along an optical axis;
   a haptic coupled with the adjustable optic and adapted to transfer forces from a capsular bag to the optic; and
   a surface adherent on at least a portion of the optic and/or haptic, wherein the surface adherent comprises a plurality of microfibers, wherein the plurality of microfibers have a diameter between 3 and 5 microns and length between 30 and 130 microns, and wherein the plurality of microfibers are configured such that orthogonal contact occurs between the plurality of microfibers and a surface of the capsular bag.

2. The accommodating intraocular lens of claim 1, wherein the haptic includes a plurality of haptic legs that extend outward to form an outer portion with the plurality of microfibers provided only on the outer portion thereof.

3. The accommodating intraocular lens of claim 2, wherein the haptic legs include disk-shaped outer ends which are flexible to conform to an interior of a capsular bag.

4. The accommodating intraocular lens of claim 1, wherein the haptic includes a vaulted structure with dual optics and a plurality of haptic legs extending outward from each and joining at convex outer ends.

5. The accommodating intraocular lens of claim 4, wherein the surface adherent is a surface having a plurality of microfibers thereon.

6. The accommodating intraocular lens of claim 5, wherein the plurality of microfibers is provided on the convex outer ends of the haptic legs.

* * * * *